United States Patent [19]
Errington

[11] Patent Number: 6,027,909
[45] Date of Patent: Feb. 22, 2000

[54] BACILLUS STRAIN AND SPORULATION ASSAY METHOD

[75] Inventor: Jeffery Errington, Oxford, United Kingdom

[73] Assignee: Isis Innovation Limited, Oxford, United Kingdom

[21] Appl. No.: 08/945,856

[22] PCT Filed: Jun. 14, 1996

[86] PCT No.: PCT/GB96/01416

§ 371 Date: Nov. 7, 1997

§ 102(e) Date: Nov. 7, 1997

[87] PCT Pub. No.: WO97/00325

PCT Pub. Date: Jan. 3, 1997

[30] Foreign Application Priority Data

Jun. 14, 1995 [GB] United Kingdom .................... 9512109

[51] Int. Cl.[7] ...................................... C12Q 1/18
[52] U.S. Cl. .................. 435/32; 435/6; 435/41; 435/69.8; 435/243; 435/252.3; 435/252.31; 435/172.1
[58] Field of Search .................... 435/6, 32, 41, 435/69.8, 243, 252.3, 252.31, 172.1

[56] References Cited

PUBLICATIONS

L. Juan Wu et al., "*Bacillus subtilis* SpoIIIE Protein Required for DNA Segregation During Asymmetric Cell Division", Science, vol. 264, Apr. 22, 1994, pp. 572–575.

D. Foulger et al., "The Role of the Sporulation gene spoIIIE in the Regulation of Prespore–specific Gene Expression in *Bacillus subtilius* ", Molecular Microbiology, vol. 3, No. 9, 1989, pp. 1247–1255.

W. Haldenwang, "The Sigma Factors of *Bactillus subtilis* ", Microbiological Reviews, vol. 59, No. 1, Mar. 1995, pp. 1–30.

D. Sun et al., "Effect of Chromosome Location of *Bacillus subtilis* Forespore Genes on Their spo Gene Dependence and Transcription by $E\sigma^f$: Identification of Features of Good $E\sigma^F$–Dependent Promoters".

*Primary Examiner*—James C. Housel
*Assistant Examiner*—Jennifer Graser
*Attorney, Agent, or Firm*—Wenderoth, Lind & Ponack, L.L.P.

[57] ABSTRACT

Mutations in the spoIII gene of *B. subtilis* abolish sporulation by preventing partition of a prespore chromosome into the small polar prespore compartment. The invention provides a Bacillus strain having a chromosome with two reporter genes each linked to a promoter and responsive to the action of $\sigma^F$ during sporulation, one located inside and the other located outside a segment of the DNA that is trapped in a prespore compartment; and use of the strain in a method of determining whether an agent inhibits SpoIIIE function in Bacillus species.

12 Claims, 2 Drawing Sheets

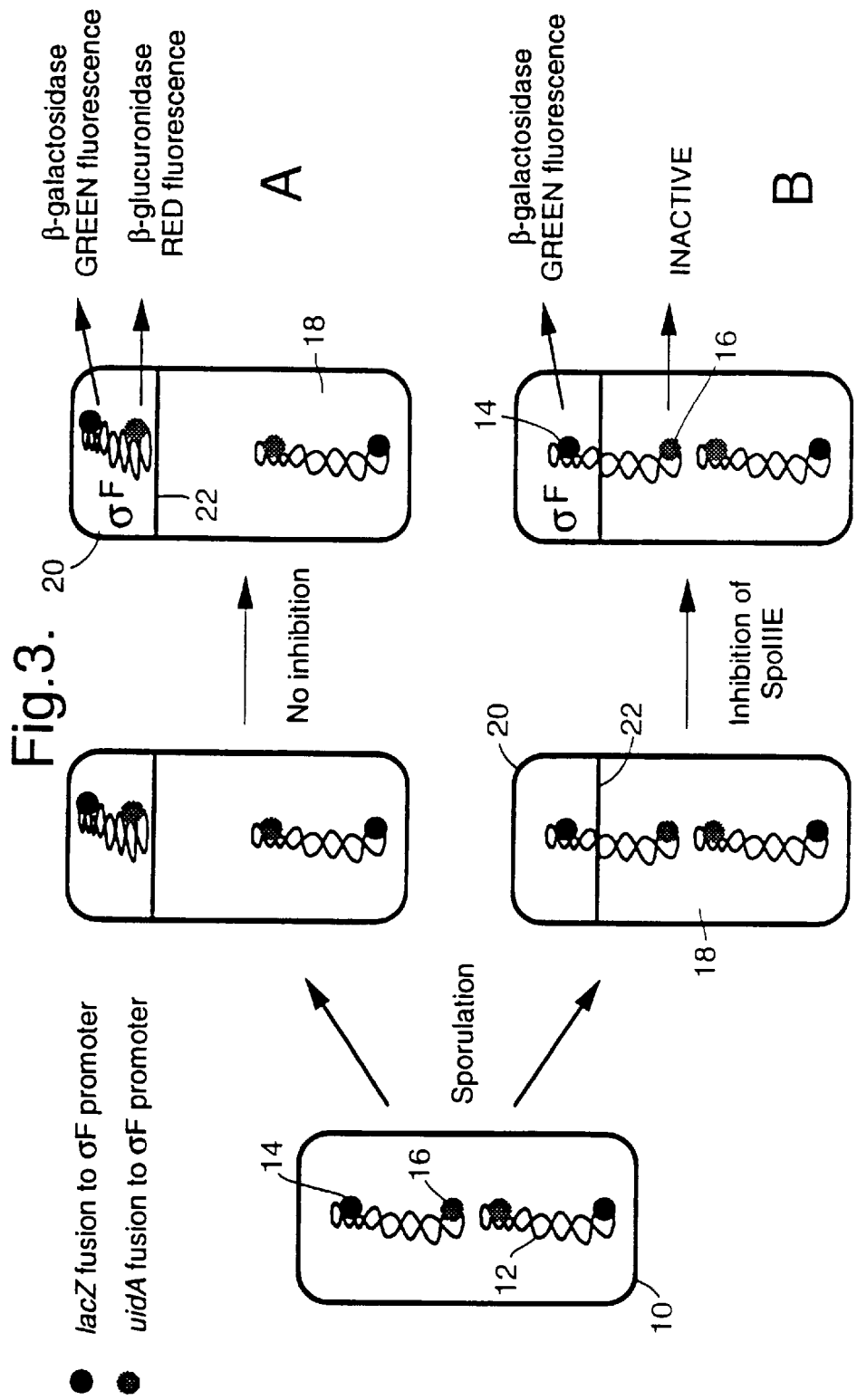

BACILLUS STRAIN AND SPORULATION ASSAY METHOD

This application claims priority under 35 USC § 371 from PCT/GB96/01416, filed Jun. 14, 1996.

BACKGROUND

Mutations in the spoIIIE gene of *B. subtilis* were first identified by their effects on sporulation, which they completely abolish (1). Although earlier work had suggested that SpoIIIE was involved in the regulation of gene expression during sporulation (2), we recently found that the primary defect in spoIIIE mutant cells lay in their failure to partition the prespore chromosome into the small, polar prespore compartment (3). In the mutant, only a small portion of the prespore chromosome (approximately 30%) enters the prespore; the remainder being left in the mother cell. The effects of the classical spoIIIE36 mutation on gene expression during sporulation could be explained by supposing that the mutation prevents genes from entering the prespore compartment. The model for SpoIIIE action presented by Wu et al (3) also explains the curious chromosome position effect that had previously been described for the effects of the spoIIIE36 mutation on gene expression (4). It seems that the small segment of DNA that enters the prespore compartment in the mutant is a specific one, so genes placed in this region are expressed normally. The same reporter gene, placed elsewhere in the chromosome is completely inactive, because the gene fails to gain access to the prespore.

As far as we know, no other mutations give rise to a spoIIIE-like phenotype. Functional studies of the protein suggest that it acts by forming a pore-like channel in the nascent spore septum, through which the prespore chromosome is driven in by a conjugation like mechanism (5). Although spoIIIE mutations have no obvious effect on vegetative growth, recent work in this laboratory has revealed that the protein can operate in vegetative cells if the normal machinery of chromosome segregation fails (6). This machinery works, in an as yet ill-defined manner, to separate the products of a round of DNA replication before the septum forms. However, if replication is delayed, e.g. by the action of an inhibitor such as nalidixic acid, the septum can close around the incompletely replicated nucleoid. In the presence of a functional spoIIIE gene, such cells can recover from this state, and the sister nucleoids eventually come to lie either side of the division septum. spoIIIE mutant cells with nucleoids trapped by septa can not recover and the nucleoid seems to be permanently trapped (6). In *B. subtilis* the spoIIIE defect is manifested in a reduction of about 2-fold in the resistance to drugs such as nalidixic acid and mitomycin C (6).

The finding of a vegetative role for SpoIIIE probably explains why the gene appears to be exceedingly well conserved in diverse members of the eubacteria (e.g. *Coxiella burnetii*, (7) and *Campylobacter jejuni*, (8)). Although its role is normally subsidiary to the primary partitioning machinery in vegetative *B. subtilis*, it may be that it has a more important role in other bacteria. In particular, we might predict a more important role for this function in bacteria in which the nascent nucleoids are more likely to be trapped by septa in normal conditions, such as in cocci and shorter rods. At least one preliminary report on Enterococcus appears to support this idea.

Figure 1:
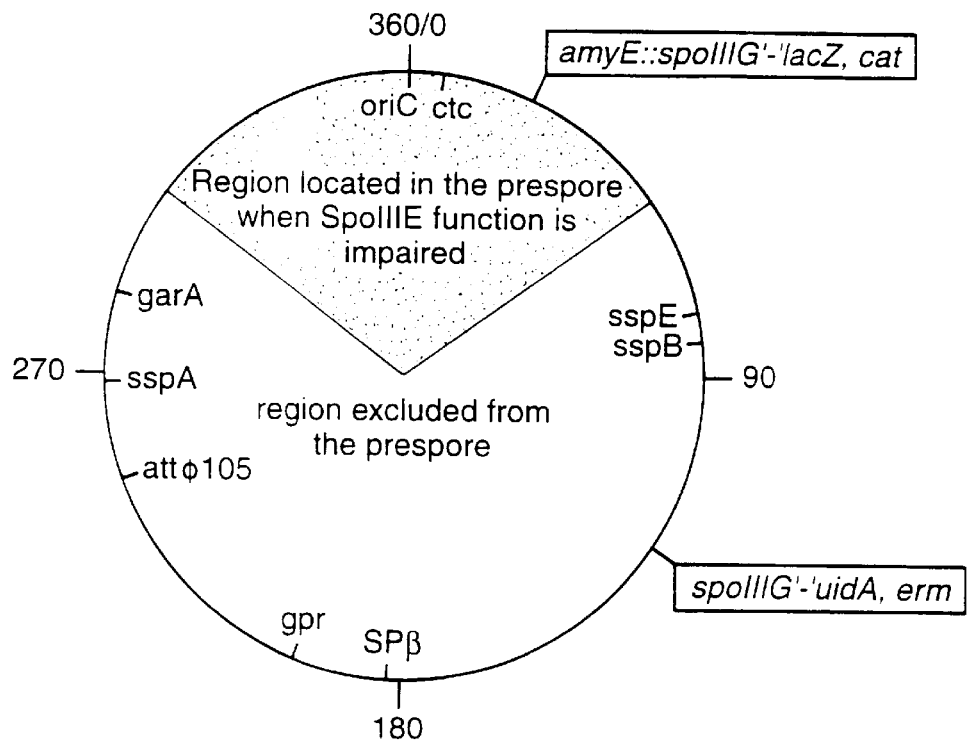
FIG. 1

Chromosome map of *B. subtilis* strain 1206, showing the two reporter gene insertions. Both reporter genes are linked to the spoIIIG promoter. One has lacZ as the reporter and is located at the amyE locus, where the gene is trapped in the prespore compartment even in the presence of a spoIIIE mutation. The other has uidA as the reporter and is located in the normal spoIIIG position. This lies outside the region that enters the prespore in spoIIIE mutants (Wu and Errington, 1994). Note that the latter fusion is an insertion in the spoIIIG gene, which disrupts the gene and hence abolishes sporulation.

FIG. 2

Effect of a spoIIIE36 mutation on synthesis of β-galactosidase and β-glucuronidase. Strain 1206 and a derivative carrying the spoIIIE36 mutation (1207) were induced to sporulate and samples were assayed for the two enzymes. Open symbols indicate time courses for the wild-type strain (1206) and filled symbols for the spoIIIE36 mutant strain (1207). Squares indicate β-galactosidase activity (from the lacZ reporter gene) and circles β-glucuronidase (from the uidA reporter gene).

FIGS. 3A and 3B

Flow chart showing an assay method according to the invention.

THE INVENTION

The unique sporulation phenotype arising when SpoIIIE is inactivated provides the potential for a very powerful and specific assay. In the absence of functional SpoIIIE, the chromosome is trapped partially inside and partially outside the prespore compartment, but the prespore-specific transcription factor, $\sigma^F$, is activated normally. Reporter genes dependent on $\sigma^F$ are expressed if they are located at certain places in the chromosome and blocked if they lie elsewhere.

In one aspect the invention provides a Bacillus strain having a chromosome with two reporter genes each linked to a promoter and responsive to the action of $\sigma^F$ during sporulation, a first reporter gene being located in a segment of the DNA that is trapped in a prespore compartment when SpoIIIE function is impaired, and a second reporter gene being located outside the said segment.

In another aspect, the invention provides a method of determining whether an agent inhibits SpoIIIE function in Bacillus species, which method comprises inducing the Bacillus strain as defined to sporulate in the presence of the agent, and observing expression of the first and the second reporter genes. It is thought that the property, of inhibiting SpoIIIE function in Bacillus species, is indicative of actual or potential anti-microbial properties in the agent. The method is thus expected to be useful for screening possible anti-microbial agents.

Any Bacillus species may be used that is capable of sporulating under suitable conditions and for which genetic constructions can be made. *B. subtilis* is conveniently accessible and well characterised and is preferred.

The Bacillus strain constructed has a chromosome with two reporter genes each linked to a promoter and responsive to the action of $\sigma^F$ during sporulation. A reporter gene is one which on expression gives rise to an easily detected or observed phenotype. For example, the expressed protein may be an enzyme which acts on a substrate to give a product that is easily observed e.g. because it is coloured or chemiluminescent or fluorescent. Reporter genes capable of being expressed in Bacillus species are well known and documented in the literature. Reporter genes are preferably chosen so that their products can be readily assayed simultaneously. lacZ has been used for more than 10 years with great success in *B. subtilis*. There are a range of useful substrates that generate coloured or fluorescent products upon hydrolysis by β-galactosidase. The uid gene of *E. coli* has recently been harnessed for similar purposes, and the range of substrates available for the gene product, β-glucoronidase, is similar to that of β-galactosidase.

In the example below, two different fluorogenic substrates are used to assay the activities of the two reporters simultaneously in a single reaction.

Each reporter gene is functionally linked to a promoter which is responsive to the action of the prespore-specific transcription factor $\sigma^F$ during sporulation. The same promoter may conveniently be used for both reporter genes, although this is not necessary. Suitable promoters include those of the gpr and spoIIIG genes.

Of the two reporter genes, the first is located in a segment of the DNA that is trapped in a prespore compartment when SpoIIIE function is impaired, while the second is located outside that segment. Reference is directed to FIG. 1 of the accompanying drawings which is a chromosome map showing the trapped segment as a shaded region extending from 10 o'clock to 2 o'clock. For a fuller discussion, reference is directed to Wu et al (3).

The assay method of the invention involves inducing the Bacillus strain described to sporulate in the presence of a putative anti-microbial agent. To screen potential inhibitors on a large scale, samples of the Bacillus strain may be cultured in the wells of a microtitre plate in an exhaustion medium to stimulate sporulation. Thereafter, observation is made of expression of the first and second reporter genes. For example, when the expression products of the two reporter genes are different enzymes, substrates for the two enzymes may be added to the wells of the microtitre plate, and observation made of e.g. chemiluminescent or fluorescent or coloured products of enzymatic activity.

Reference is directed to FIG. 3 of the accompanying drawings, which is a flow chart showing an assay method according to the invention. A *B. subtilis* cell 10 contains two copies of a chromosome 12 having two reporter gene insertions: a lacZ gene shown as a black filled circle 14, and a uidA gene shown as a shaded circle 16, both fused to a $\sigma^F$ promoter. Sporulation causes the cell to divide into two compartments, a mother cell compartment 18 and a prespore compartment 20, separated by a septum 22. The sporulation process follows one of two routes A and B. In route A, the functional spoIIIE gene causes the complete chromosome to enter the prespore compartment. In route B, the spoIIIE gene is defective or its product has been inhibited as a result of contact with an anti-microbial agent, and only a small proportion (about 30%) of the chromosome enters the prespore compartment.

The prespore-specific transcription factor $\sigma^F$ causes expression of genes in the prespore compartment 20 but not the mother cell compartment 18. In route A, this results in production of β-galactosidase (from the lacZ gene) and β-glucoronidase (from the uidA gene). In route B, only the β-galactosidase, and not the β-glucoronidase, is produced. After sporulation, the cells are lysed, e.g. with lysozyme so as not to inactivate the enzymes, and fluorogenic substrates for the two enzymes are added. The presence of either or both enzymes may be detected simultaneously by a fluorimeter set to receive two different appropriate wavelengths for the fluorescent products of enzymic activity.

In the absence of inhibition of SpoIIIE, both reporter genes are active and both fluorescent products are made. Inhibitors that act non-specifically preventing sporulation or otherwise preventing $\sigma^F$ from becoming active, eliminate both activities and neither fluorescent product is made. A specific inhibitor of SpoIIIE, would have no effect on activation of $\sigma^F$ but it would prevent it from directing transcription of one of the reporters, so only one of the fluorescent products would be made. A substance (a putative anti-microbial agent) which alters the ratio of the two fluorescences can be re-tested in more detail.

EXAMPLE

*B. Subtilis* strain 1206 has two reporter genes that are responsive to the action of $\sigma^F$ during sporulation (FIG. 1). A spoIIIG'-'lacZ fusion marked with a selectable chloramphenicol resistance gene (cat) has been placed at the amyE locus. This locus lies within the segment of DNA that is trapped in the prespore when SpoIIIE function is impaired (Wu et al, 1994). This fusion should be available for transcription directed by the prespore-specific sigma factor $\sigma^F$, even when SpoIIIE function is impaired. The second reporter gene is a spoIIIG'-uidA fusion, tagged with an erythromycin resistance gene, erm. This fusion is placed in the spoIIIG locus, which lies outside the segment of DNA trapped in the prespore in spoIIIE mutants (FIG. 1). Its expression should thus be blocked when SpoIIIE function is impaired.

Figure 2:
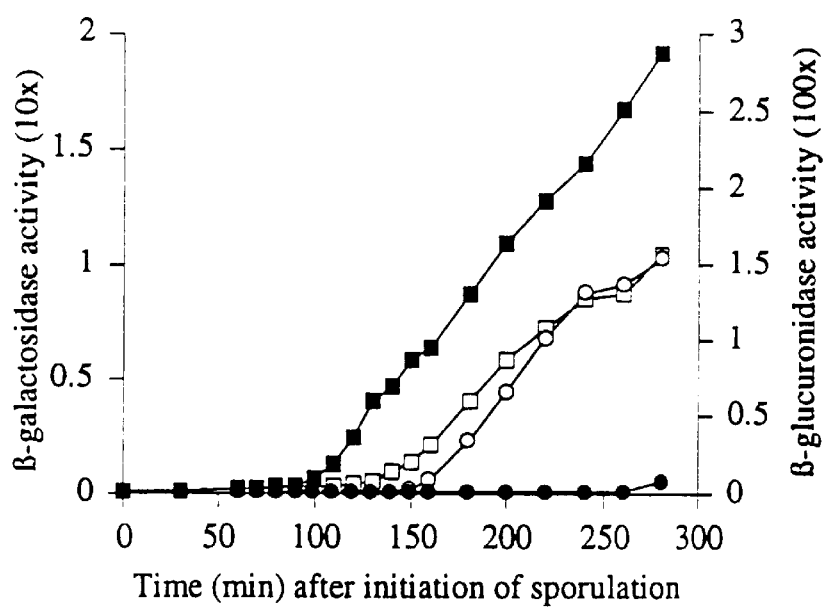

In a spoIIIE[30] strain of *B. subtilis* (strain 1206) these fusions are both strongly induced soon after the onset of sporulation (FIG. 2). This is expected because $\sigma^F$ is activated normally in the prespore where both reporter genes are available. The fusion to lacZ giving β-galactosidase activity, is still expressed in the presence of the spoIIIE36 mutation (strain 1207), which blocks SpoIIIE function. However, synthesis of β-glucoronidase is abolished because the fusion to uidA fails to enter the prespore compartment, where $\sigma^F$ activation has occurred. We do not understand why β-galactosidase activity is higher and appears sooner in the presence of the spoIIIE36 mutation but this only serves to emphasise the difference between the behaviour of the two strains.

These results show that strain 1206 provides a sensitive assay strain with which to identify compounds that specifically impair SpoIIIE function. Such compounds would result in production of β-glucoronidase. The ratio of these two enzymes could be measured conveniently in a single assay mixture as outlined above.

REFERENCES

1. Piggot, P J and J G Coote, 1976. Genetic aspects of bacterial endospore formation. Bact. Revs., 40:908–962.
2. Foulger, D and J Errington, 1989. The role of the sporulation gene spoIIIE in the regulation of prespore-specific gene expression in *Bacillus subtilis*. Mol. Microbiology, 3:1247–1255.
3. Wu, L J and J Errington, 1994. *Bacillus subtilis* SpoIIIE protein required for DNA segregation during asymmetric cell division. Science 264:572–575.
4. Sun, D, P Fajardo-Cavazos, M D Sussman, F Tovar-Rojo, R M Cabrera-Martinez, and P Setlow, 1991. Effect of chromosome location of *Bacillus subtilis* gene dependence and transcription by E$\sigma^F$: identification of features of good E$\sigma^F$-dependent promoters. J. Bacteriol. 173:7867–7874.

5. Wu, L J, P J Lewis, R Allmansberger, P Hauser and J Errington, 1995. A conjugation-like mechanism for prespore chromosome partitioning during sporulation in *Bacillus subtilis*. Genes and Development (in press).

6. Sharpe, M E and J Errington, 1995. Post-septational mechanism of chromosome partitioning in bacteria. PNAS (in press).

7. Oswald, W and D Thiele, 1993. A sporulation gene in *Coxiella burnetii*. J Vet Med, B 40:366–370.

8. Miller, S E C Pesci and C L Pickett, 1994. Genetic organisation of the region upstream from the *Campylobacter jejuni* flagellar gene fihA. Gene, 146:31–38.

I claim:

1. A Bacillus strain having a functional SpoIIIE gene, and having a chromosome with first and second reporter genes which reporter genes are different, each reporter gene being linked to a promoter such that said reporter genes are responsive to the action of $\sigma^F$ during sporulation, said first reporter gene being located in a segment of DNA that is trapped in a prespore compartment when SpoIIIE function is impaired, and said second reporter gene being located outside said segment.

2. A Bacillus strain as claimed in claim 1 wherein each reporter gene is linked to the same promoter.

3. A Bacillus strain as claimed in claim 2, wherein the promoter is spoIIIG.

4. A Bacillus strain as claimed in claim 1, wherein the reporter genes are lacZ and uidA.

5. A Bacillus strain as claimed in claim 1, which is a *B. subtilis* strain.

6. A method of determining whether an agent inhibits SpoIIIE function in Bacillus species, which method comprises inducing the Bacillus strain as claimed in claim 1 to sporulate in the presence of the agent, and observing expression of the first and second reporter genes, wherein an agent which diminishes expression of the second reporter gene relative to the first reporter gene is indicative of an agent which inhibits SpoIIIE function and has antimicrobial properties.

7. A method as claimed in claim 6, wherein the two reporter genes are expressed as enzymes, the activities of which are observed by fluorimetry.

8. A method as claimed in claim 7, wherein samples of the Bacillus strain are cultured in the wells of a microtitre plate in an exhaustion medium to stimulate sporulation, and then the cells are lysed and fluorogenic substrates for the two enzymes are added to the wells.

9. A method which comprises inducing the Bacillus strain as claimed in any one of claims 1 to 5, to sporulate in the presence of an agent, observing expression of the first and second reporter genes and thereby determining that the agent inhibits SpoIIIE function in the Bacillus species, and using the agent as an antimicrobial agent to kill or control the growth of bacteria, wherein an agent which diminishes expression of the second reporter gene relative to the first reporter gene is indicative of an agent which inhibits SpoIIIE functional and has antimicrobial properties.

10. A method of killing bacteria or inhibiting the growth of bacteria which method comprises contacting the bacteria with a substance which inhibits SpoIIIE function in the Bacillus strain according to claim 1.

11. A method for identifying an agent having antimicrobial properties, which comprises adding said agent to a Bacillus strain as claimed in any one of claims 1 to 5, inducing said Bacillus strain to sporulate, and observing expression of the first and second reporter genes, wherein an agent which diminishes expression of the second reporter gene relative to the first reporter gene is indicative of an agent which inhibits SpoIIIE function and has antimicrobial properties.

12. A method of making a Bacillus strain as claimed in any one of claims 1 to 5, which comprises inserting a first reporter gene in a segment of chromosomal DNA that is trapped in the prespore compartment when SpoIIIE function is impaired, and inserting a second reporter gene which is different from said first reporter gene in a segment of chromosomal DNA that is located outside the prespore compartment when SpoIIIE function is impaired.

* * * * *